US010149940B2

(12) United States Patent
Yagi et al.

(10) Patent No.: US 10,149,940 B2
(45) Date of Patent: Dec. 11, 2018

(54) CONNECTOR FOR FLUID, AND SYRINGE

(71) Applicant: NIPRO CORPORATION, Osaka-shi, Osaka (JP)

(72) Inventors: Hideki Yagi, Osaka (JP); Naoaki Yasumura, Osaka (JP)

(73) Assignee: NIPRO CORPORATION, Osaka-shi (JP)

( * ) Notice: Subject to any disclaimer, the term of this patent is extended or adjusted under 35 U.S.C. 154(b) by 284 days.

(21) Appl. No.: 14/904,261

(22) PCT Filed: Jul. 9, 2013

(86) PCT No.: PCT/JP2013/068729
§ 371 (c)(1),
(2) Date: May 9, 2016

(87) PCT Pub. No.: WO2015/004728
PCT Pub. Date: Jan. 15, 2015

(65) Prior Publication Data
US 2016/0250415 A1    Sep. 1, 2016

(51) Int. Cl.
*A61M 25/16* (2006.01)
*A61M 25/18* (2006.01)
(Continued)

(52) U.S. Cl.
CPC .............. *A61M 5/31* (2013.01); *A61M 39/10* (2013.01); *A61M 39/1011* (2013.01);
(Continued)

(58) Field of Classification Search
CPC ...... A61M 39/1011; A61M 2039/1027; A61M 2039/1033; A61M 2039/1038;
(Continued)

(56) References Cited

U.S. PATENT DOCUMENTS 5,135,489 A    8/1992   Jepson et al.
6,196,998 B1 *  3/2001   Jansen ................ A61M 5/3134
                                                           604/111

(Continued)

FOREIGN PATENT DOCUMENTS

EP    2182265 A1    5/2010
JP    H03-504571 A  10/1991
(Continued)

OTHER PUBLICATIONS

Oct. 15, 2013 Search Report issued in International Patent Application No. PCT/JP2013/068729.
(Continued)

*Primary Examiner* — Rebecca E Eisenberg
(74) *Attorney, Agent, or Firm* — Oliff PLC

(57) ABSTRACT

A connector which is detachably connected to a cylindrical section is prevented from unintentionally disconnecting and breaking. The connector has inner and outer cylinder members. The inner cylinder member has an engagement plate protruding from the inner peripheral surface of an inner cylinder body and engaging with a recess formed in the outer peripheral surface of the cylindrical section, and also has slits arranged radially and extending from the engagement plate to a part of the inner cylinder body. The engagement between the recess and the engagement plate restricts the axial movement of the inner cylinder member relative to the cylindrical section. When the outer cylinder member is mounted on the inner cylinder member, the inner peripheral surface of the outer cylinder member is in contact with the outer peripheral surface of the inner cylinder member, and the displacement of the engagement plate in the diameter expansion direction is restricted.

11 Claims, 14 Drawing Sheets

(51) Int. Cl.
*A61M 39/00* (2006.01)
*A61M 39/10* (2006.01)
*A61M 5/31* (2006.01)

(52) U.S. Cl.
CPC ............... *A61M 2039/1027* (2013.01); *A61M 2039/1033* (2013.01); *A61M 2039/1038* (2013.01); *A61M 2039/1077* (2013.01)

(58) Field of Classification Search
CPC .......... A61M 2039/1077; A61M 39/10; A61M 2039/1066; A61M 2039/1072; A61M 2039/1083; A61M 2039/269; A61M 25/0097
See application file for complete search history.

(56) References Cited

U.S. PATENT DOCUMENTS

| | | | |
|---|---|---|---|
| 2003/0163093 A1 | 8/2003 | Thibault et al. | |
| 2011/0015580 A1* | 1/2011 | Stroup | A61M 5/16881 604/207 |
| 2012/0065626 A1 | 3/2012 | Naftalovitz et al. | |
| 2012/0116355 A1 | 5/2012 | Heinz et al. | |
| 2012/0130352 A1 | 5/2012 | Naftalovitz et al. | |
| 2012/0157928 A1* | 6/2012 | Mermet | A61M 5/344 604/187 |
| 2015/0283372 A1* | 10/2015 | Maritan | A61M 39/10 604/187 |
| 2016/0143811 A1* | 5/2016 | Poncon | A61M 5/344 604/404 |
| 2016/0361497 A1* | 12/2016 | Swisher | A61M 5/31 |
| 2017/0290984 A1* | 10/2017 | Bosshardt | A61M 5/24 |

FOREIGN PATENT DOCUMENTS

| | | |
|---|---|---|
| JP | 2004-513675 A | 5/2004 |
| JP | 4599875 B2 | 12/2010 |
| JP | 2012-521256 A | 9/2012 |
| WO | 2010/124676 A1 | 11/2010 |
| WO | 2014/057071 A1 | 4/2014 |

OTHER PUBLICATIONS

Apr. 3, 2017 Extended Search Report issued in European Patent Application No. 13889195.7.

* cited by examiner

CONNECTOR FOR FLUID, AND SYRINGE

TECHNICAL FIELD

The present invention relates to a connector for a fluid, in which a connection member is detachably attached to a cylindrical section through which a fluid passes, and relates to a syringe having such a connector for fluid.

BACKGROUND ART

In a medical site, syringes are connected to needles, catheters, administration sets, and the like while being used, and catheters are connected to other catheters, administration sets, and the like while being used. As a method of connecting a medical instrument with another medical instrument, for example, there is a method of simply inserting a cylindrical section such as an aperture section of a syringe into inside the counterpart instrument, in such a manner as to fit a male luer taper formed on the outer peripheral surface at the leading end portion of the aperture section, together with a female luer taper formed on the inner peripheral surface of the counterpart instrument. Another example method of connecting a medical instrument with another medical instrument is a method of connecting a counterpart instrument with an inner peripheral surface of a substantially cylindrical connection member (luer lock adaptor) which is provided for accommodating therein the cylindrical section (e.g., by screw-fastening a female screw on the inner peripheral surface of the connection member with a male screw of the counterpart instrument), in addition to the connection by the luer tapers.

To enable any of the two connection methods to be used, there are medical instruments each having a fluid connector having a cylindrical section and a connection member that allow attachment and detachment of a cylindrical section. For example, a connection member of a syringe in PTL 1 includes two arms, and a hook portion at the leading end of each arm, which engages with a recess provided on the outer peripheral surface of a body portion of the syringe main body to keep the connection member on the syringe main body. To detach the connection member from the syringe main body, the trailing end of the arms are pressed to move the leading ends of the arms away from each other.

Search Report for Prior Art Documents
Patent Literature
[PTL 1] Japanese Patent No. 4599875

SUMMARY OF THE INVENTION

Technical Problem

However, with the above syringe of PTL 1, the connection member may unintentionally disconnected, when the trailing ends of the arms of the connection member are held by a hand or when the trailing ends of the arms hits another instrument. Further, the arms are lengthy stick members and are uncovered. Therefore, there is a chance of breaking the arms by having them hit the other instruments.

To address the issue, it is an object of the present invention to provide a connector for a fluid, in which a connection member thereof is prevented from unintentional disconnection and breakage, and to provide a syringe having such a connector.

Technical Solution

A first aspect of the present invention is a connector for a fluid, comprising: a cylindrical section configured to let a fluid pass therethrough, which has a male luer taper at a distal end portion of its outer peripheral surface; a connection member detachably attached to the cylindrical section, which is used in connecting with another member having, on its inner peripheral surface, a female luer taper, wherein the cylindrical section has, on an outer peripheral surface of a proximal other end portion, an annular recess, wherein the connection member comprises an inner cylinder member coaxial with the cylindrical section, which is mountable to the cylindrical section in such a manner that the cylindrical section is at least partially accommodated inside the inner cylinder member, and an outer cylinder member which is coaxial with the inner cylinder member, and which is mountable to the inner cylinder member in such a manner that the inner cylinder member is at least partially accommodated inside the outer cylinder member, the outer cylinder member being fittable with the inner cylinder member in such a manner that the outer cylinder member is moved from the distal end portion of the cylindrical section toward the proximal other end portion of the cylindrical section with respect to the inner cylinder member mounted to the cylindrical section, wherein the inner cylinder member comprises an inner cylinder body having on its inner peripheral surface a female screw, and an engagement plate configured to engage with the annular recess and connect with the inner cylinder body at a position farther from the distal end portion of the cylindrical section than the female screw is from the distal end portion, relative to an axial direction of the cylindrical section, wherein the inner cylinder member is provided with a plurality of slits which are arranged radially with respect the axial direction of the cylindrical section, and which extend from the engagement plate to a part of the inner cylinder body so as to divide the engagement plate into a plurality of engagement pieces, and partially divide the inner cylinder body into segments corresponding to the plurality of engagement pieces, wherein a movement of the inner cylinder member in an axial direction of the cylindrical section relative to the cylindrical section is restricted by engagement of the annular recess with the engagement plate, wherein, when the outer cylinder member is not mounted to the inner cylinder member, the plurality of engagement pieces are displaceable in diameter expansion directions as a result of elastic deformation of the inner cylinder member when a radial force is applied to the engagement plate, and wherein, when the outer cylinder member is mounted to the inner cylinder member, an inner peripheral surface of the outer cylinder member contacts an outer peripheral surface of the inner cylinder member within a range of the plurality of slits, relative to an axial direction of the cylindrical section, thereby restricting displacement of the plurality of engagement pieces in the diameter expansion directions.

In the above structure, the outer cylinder member positioned outermost of the connection member is attached to the inner cylinder member by having its inner peripheral surface fit together with the inner cylinder member. Further, to detach the connection member from the cylindrical section, the outer cylinder member needs to be moved in the axial direction relative to the inner cylinder member. While the outer cylinder member is mounted to the inner cylinder member, the engagement pieces of the inner cylinder member are restricted from displacing in the diameter expansion directions, keeping the engagement pieces engaged with the recess. This prevents the inner cylinder member from being detached from the cylindrical section. Therefore, the connection member will not be detached from the cylindrical section simply by holding the connection member with a hand, or by the connection member hitting the other instrument. Therefore, unintentional disconnection of the connection member is prevented.

Further, the outer cylinder member and the inner cylinder member are less likely to be broken than traditional connection members of syringes having arms extended in the axial direction, because they do not have a portion protruding in the axial direction.

A second aspect of the present invention is the connector of the above first aspect adapted so that a bottom surface of the annular recess forms a polygonal shape when viewed in the axial direction of the cylindrical section, and movements of the inner cylinder member in a circumferential direction and in the axial direction, relative to the cylindrical section are restricted by having the annular recess engaged with the engagement plate.

With the above structure, in which a movement of the inner cylinder member relative to the cylindrical section in the circumferential direction is restricted, the female screw of the inner cylinder member is prevented from rotating along with a male screw of the other instrument, when the female screw is screw-fastened with the male screw.

A third aspect of the present invention is the connector of the above first aspect adapted so that a bottom surface of the annular recess forms a circular shape when viewed in the axial direction of the cylindrical section.

With the above structure, the inner cylinder member is rotatable relative to the cylindrical section. Thus, although, when screw-fastening the male screw of another instrument to the female screw of the inner cylinder member, the connection member needs to be held to prevent the rotation of inner cylinder member along with the male screw, it is possible to rotate the inner cylinder member to bring it to a position that facilitates screw-fastening before starting the connection work. Therefore, the connection work is made easy.

A fourth aspect of the present invention is the connector of the above first aspect adapted so that the inner peripheral surface of an outer cylinder member contacts the outer peripheral surface of the engagement plate, when the outer cylinder member is mounted to the inner cylinder member.

Since the inner peripheral surface of the outer cylinder member contacts the outer peripheral surface of the engagement plate in the above structure, the engagement plate and the recess are firmly engaged.

A fifth aspect of the present invention is the connector of the above first aspect adapted so that the inner peripheral surface of the outer cylinder member is provided with at least one engagement protrusion, and the outer peripheral surface of the inner cylinder member is provided with at least one engagement groove which engages with said at least one engagement protrusion.

In the above structure, the outer cylinder member is attached to the inner cylinder member by fitting the inner peripheral surface of the outer cylinder member together with the inner cylinder member and engaging the engagement protrusions inner cylinder member with the engagement grooves of the inner cylinder member. This makes it more difficult to detach the outer cylinder member from the inner cylinder member, as compared with cases where the outer cylinder member is attached to the inner cylinder member simply by fitting the outer cylinder member together with the inner cylinder member. Therefore, unintentional disconnection of the outer cylinder member is prevented.

A sixth aspect of the present invention is the connector of the above fifth aspect adapted so that each of the at least one engagement groove has a portion formed in a circumferential direction, and each of the at least one engagement protrusion is positioned in the portion of each of the at least one engagement groove when the outer cylinder member is mounted to the inner cylinder member.

With the above structure, while the outer cylinder member is mounted to the inner cylinder member, each of the engagement protrusions is positioned so as to be interposed in the axial directions, in the above portion of the engagement groove, the portion formed along the circumferential direction. This restricts the movement of the outer cylinder member in the axial direction relative to the inner cylinder member. Therefore, even when the outer cylinder member is pulled in the axial direction, the outer cylinder member is not detached from the inner cylinder member, and hence, unintentional disconnection of the outer cylinder member is prevented.

A seventh aspect of the present invention is the connector of the above sixth aspect adapted so that each of at least one the engagement groove has a projection which protrudes outwardly in a radial direction and is configured to face each of the at least one engagement protrusion relative to the circumferential direction when the outer cylinder member is mounted to the inner cylinder member, and the projection is designed so as to allow each of the at least one engagement protrusion to climb over the projection by moving, in the circumferential direction relative to the inner cylinder member, the outer cylinder member mounted to the inner cylinder member.

With the above structure, while the outer cylinder member is mounted to the inner cylinder member, each of the engagement protrusions faces the projection in the circumferential direction. This makes it difficult to rotate the outer cylinder member relative to the inner cylinder member, which prevents unintentional disconnection of the connection member. Further, when loosening the outer cylinder member and the inner cylinder member, each of the engagement protrusions first climbs over the projection. This provides a user a feeling of operation.

An eighth aspect of the present invention is the connector of the above fifth aspect adapted so that each of the at least one engagement groove is formed in the axial direction of the cylindrical section.

With the above structure, the outer cylinder member is detached from or attached to the inner cylinder member, simply by moving the outer cylinder member in the axial direction, relative to the inner cylinder member. Therefore, attachment and detachment are facilitated.

A ninth aspect of the present invention is the connector of the above eighth aspect adapted so that each of the at least one engagement groove has a projection which protrudes outwardly in a radial direction and is configured to face each of the at least one engagement protrusion relative to the axial direction of the cylindrical section, when the outer cylinder member is mounted to the inner cylinder member, and the projection is designed so as to allow each of the at least one engagement protrusion to climb over the projection by moving, in the axial direction of the cylindrical section relative to the inner cylinder member, the outer cylinder member mounted to the inner cylinder member.

With the above structure, while the outer cylinder member is mounted to the inner cylinder member, each of the engagement protrusions faces the projection in the axial direction. This makes it difficult to move the outer cylinder member, in the axial direction, relative to the inner cylinder member, which prevents unintentional disconnection of the connection member. Further, when loosening the outer cylinder member and the inner cylinder member, each of the engagement protrusions first climbs over the projection. This provides a user a feeling of operation.

A tenth aspect of the present invention is the connector of the above second aspect adapted so that an area surrounded by the plurality of engagement pieces has a polygonal shape when viewed in the axial direction of the cylindrical section, and the plurality of slits are formed in positions corresponding to angles of the polygonal shape.

With the above structure, the plurality of slits are provided to extend through positions corresponding to angles of a hexagon formed by the inner peripheral surface of the engagement plate. As such, the inner peripheral surface of each engagement piece forms one side of the hexagon. Since the inner peripheral surface of each engagement piece is flat, the inner cylinder member is easily manufacturable.

An eleventh aspect of the present invention is a syringe comprising: the connector for a fluid according to the above first aspect, comprising a syringe main body having a cylindrical body section having a bottom, and the cylindrical section having the proximal other end portion which connects a center of the bottom of the body section; and the connection member.

EMBODIMENTS

Embodiment 1

Figure 1:
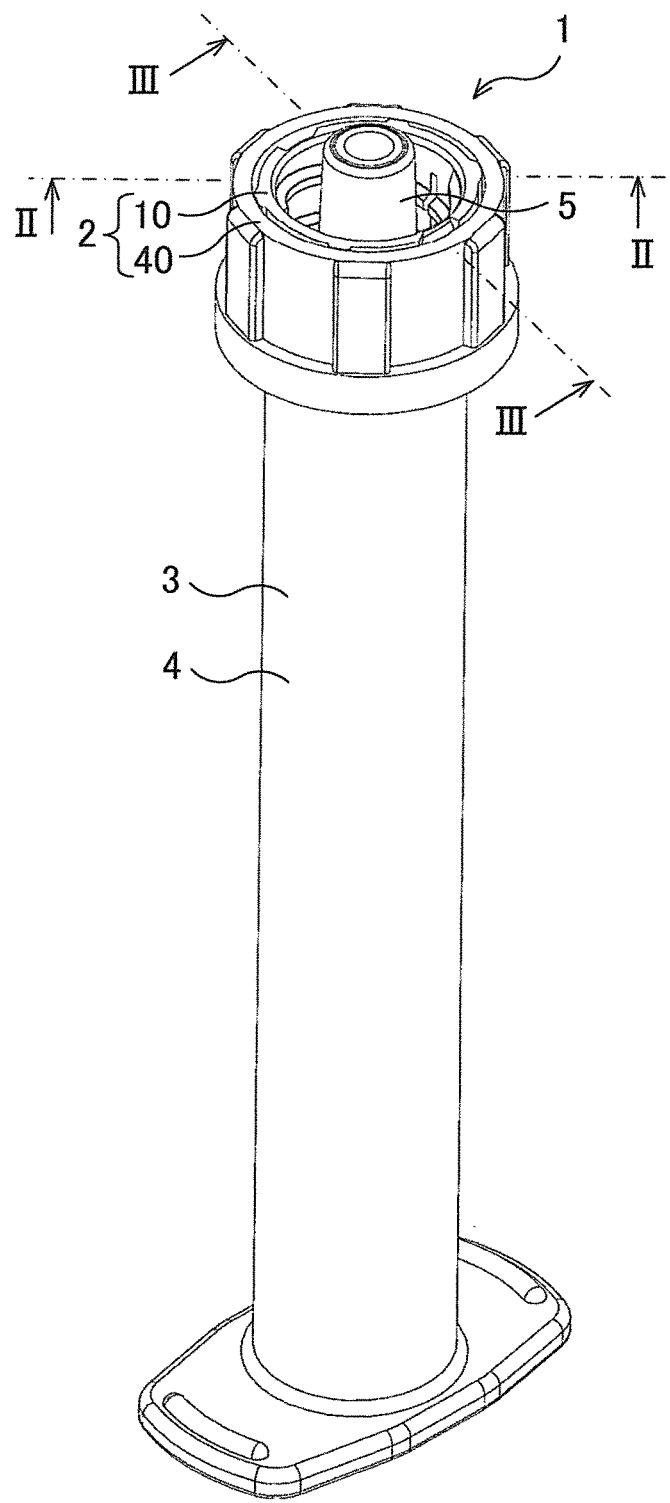
FIG. 1 is a perspective view of a syringe related to Embodiment 1 of the present invention.

The following describes Embodiment 1 of the present invention. As shown in FIG. 1, a syringe 1 of the present embodiment includes: a syringe main body 3, a connection member 2 detachably attached to the syringe main body 3, a gasket (not shown) capable of slide in the syringe main body 3, and a plunger (not shown) for moving the gasket. It should be noted that the wording "axial direction" appearing in the following description of the syringe refers to a direction parallel to the length of the syringe main body 3. Further, the top and bottom in FIG. 1 to FIG. 3, and FIG. 7 are referred to as front and back, respectively.

The syringe 1 of the present embodiment is used as a pre-filled syringe which is filled with a drug solution and the like in advance, or as a syringe for any other purposes. The syringe 1 is connected to another member (not shown) having a female luer taper on its inner peripheral surface.

The syringe main body 3 is made of a synthetic resin or glass, a cylindrical body section 4 with a bottom, and a cylindrical aperture section (cylindrical section) 5 protruding from the center of the bottom of the body section 4. By moving the plunger (not shown) towards the aperture section 5 of the syringe main body 3, the drug solution and the like in the syringe main body 3 is ejected.

Figure 2:
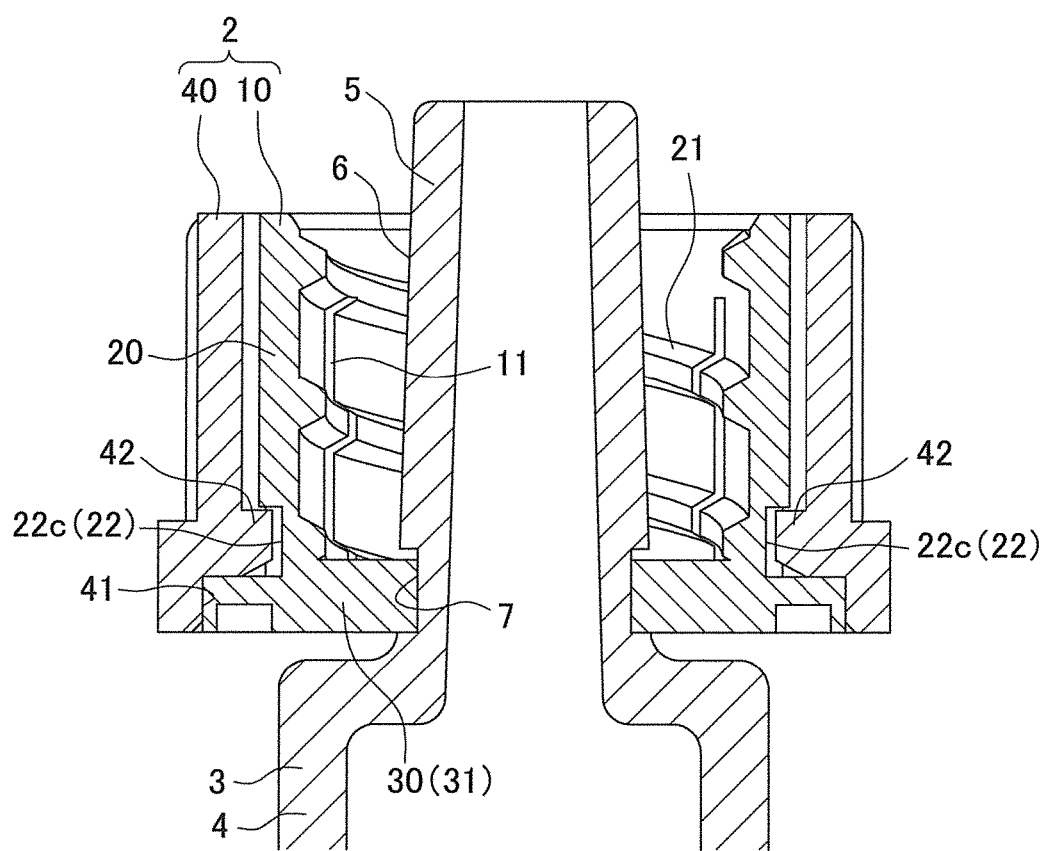
FIG. 2 is a cross sectional view taken along the line II-II of FIG. 1.
Figure 3:
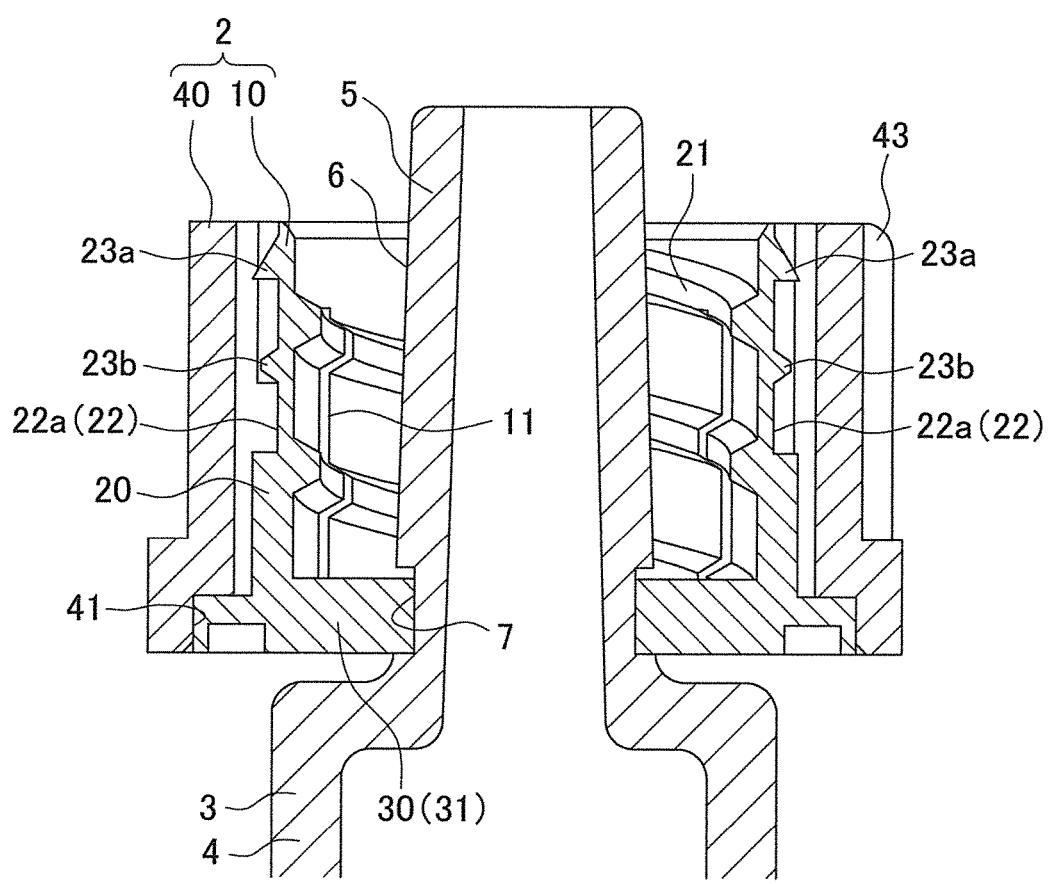
FIG. 3 is a cross sectional view taken along the line III-III of FIG. 1.
Figure 4:
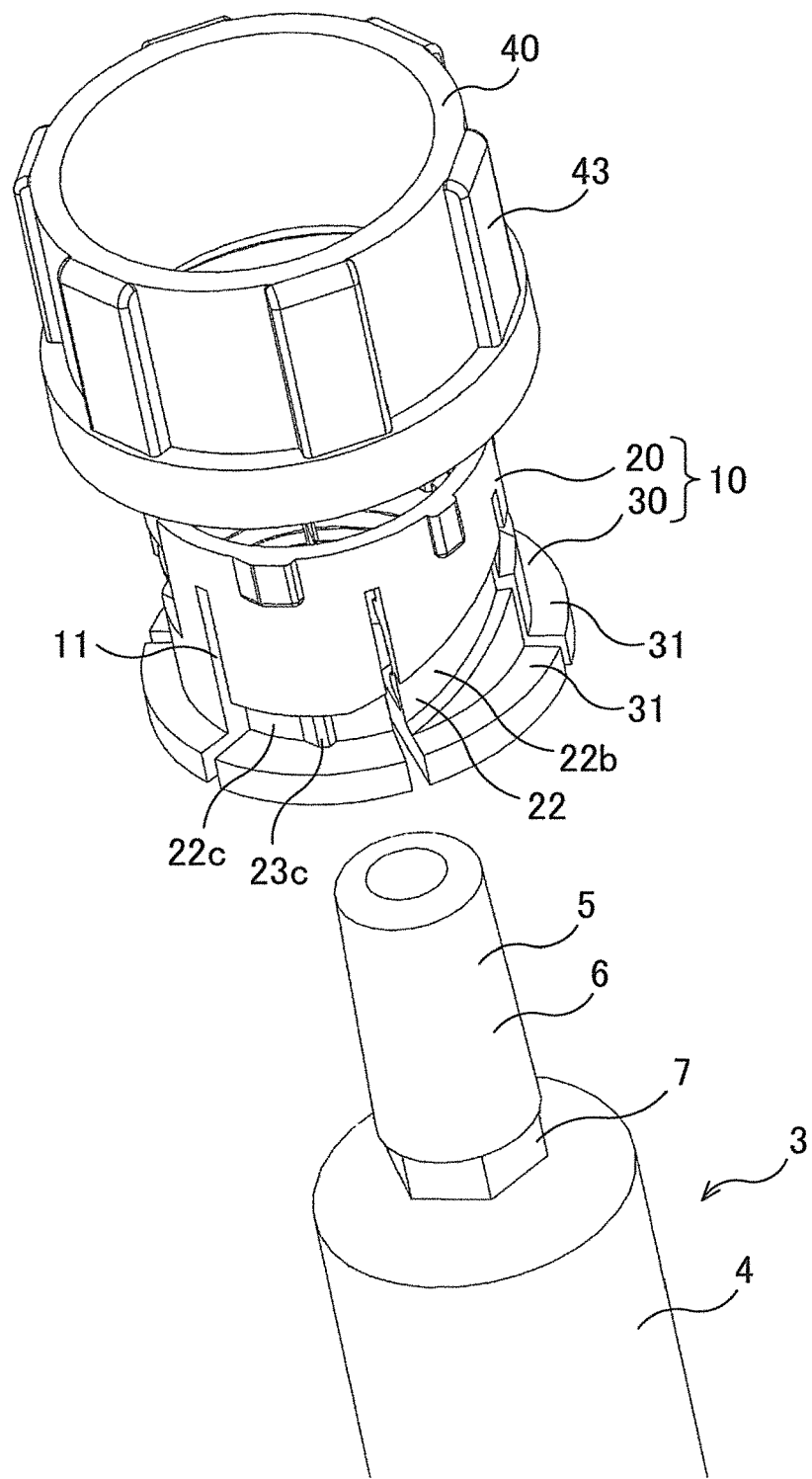
FIG. 4 is an exploded perspective view of a syringe shown in FIG. 1.

As shown in FIG. 2 and FIG. 3, the leading end of the aperture section 5 has a male luer taper 6 on its outer peripheral surface, and is tapered. The male luer taper 6 is formed so as to fit together with the female luer taper provided on the inner peripheral surface of the other member (not shown). Further, the aperture section 5 has an annular recess 7 at its outer peripheral surface, on the back side of the male luer taper 6. As shown in FIG. 4, the bottom surface of the recess 7 forms a hexagon, when viewed in the axial direction. A distance between the bottom surface and the bottom surface on the other side, of the recess 7, is shorter than the diameter of the trailing end of the male luer taper 6.

The connection member 2 is detachably attached to the aperture section 5 of the syringe main body 3. For example, the connection member 2 is used for connecting the syringe 1 to the other member (not shown) having on its inner peripheral surface a female luer taper, and having a male screw on its outer peripheral surface. When the connection member 2 obstructs the connection, the connection member 2 is detached. The connection member 2 and the aperture section 5 structure a connector of the present invention, for a fluid.

The connection member 2 is made of a synthetic resin. The connection member 2 includes an inner cylinder member 10 configured to be attached to the outer peripheral surface of the aperture section 5, and an outer cylinder member 40 configured to be attached to the inner cylinder member 10. The inner cylinder member 10 and the outer cylinder member 40 are disposed coaxially with the aperture section 5.

The inner cylinder member 10 is mounted to the aperture section 5 so as to accommodate therein the axial directional range from a portion nearby the aperture section 5 to the recess 7. The inner cylinder member 10 has a substantially cylindrical inner cylinder body 20 and an engagement plate 30 formed at the trailing end of the inner cylinder member 20. On the inner peripheral surface of the inner cylinder body 20 is provided a female screw 21 which is capable of being screw-fastened with the male screw of the other member. The engagement plate 30 has a substantially annular shape, and its inner peripheral end and outer peripheral end protruded from the inner peripheral surface and the outer peripheral surface of the inner cylinder body 20, respectively.

Figure 5:
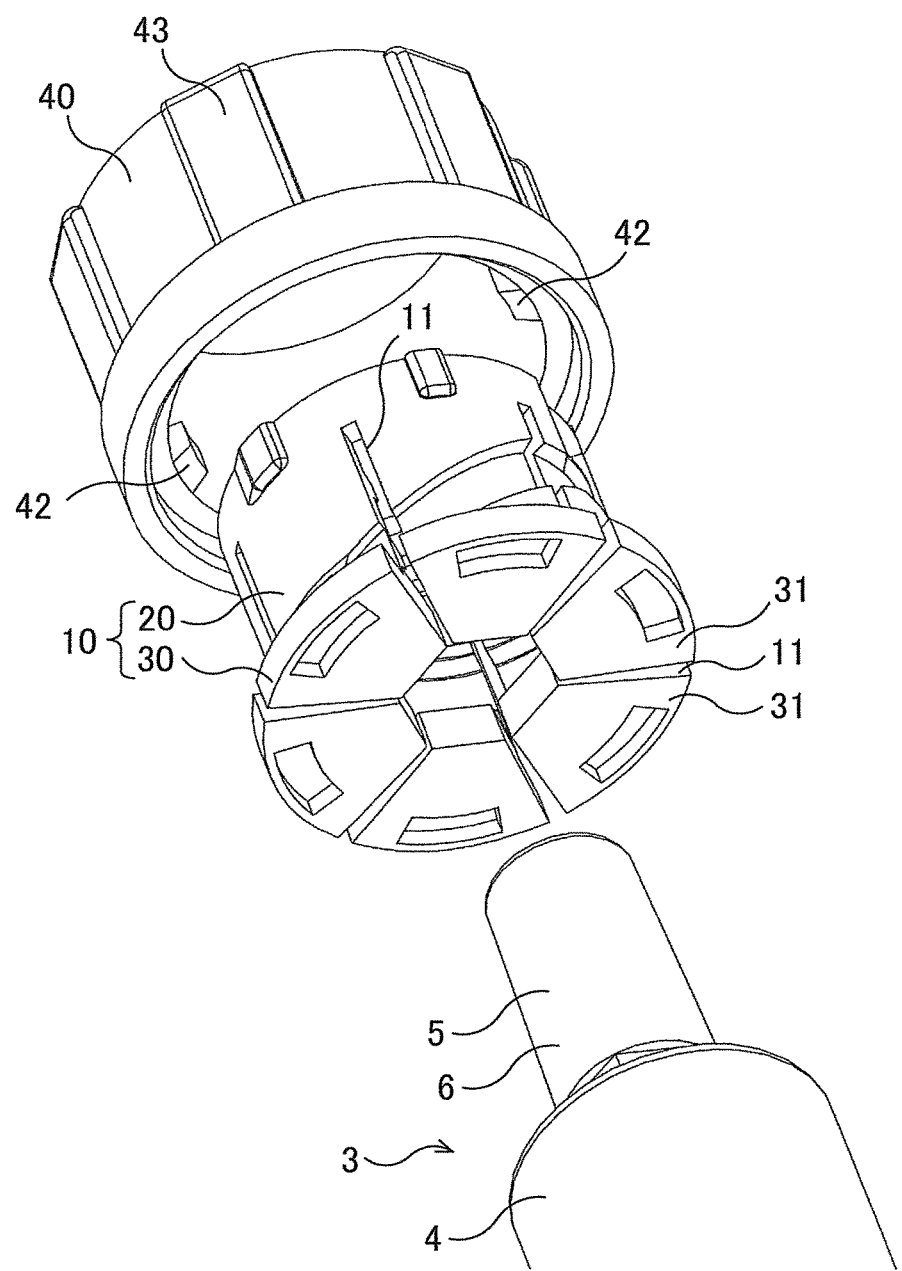
FIG. 5 is an exploded perspective view of a syringe shown in FIG. 1.

As shown in FIG. 5, the inner cylinder body 10 has six slits 11 extended in the axial direction, from the trailing end of the engagement plate 30 to a part of the inner cylinder body 20 (approximately ¾ of the entire length of the inner cylinder member 10). The six slits 11 are radially formed. With these six slits 11, the engagement plate 30 are divided into six engagement pieces 31 each having substantially a fan-shape, and the approximately ¾ of the inner cylinder body 20 is segmented into six segments. While the inner cylinder member 10 is not mounted to the aperture section 5, application of a force to the engagement plate 30 in radial directions causes elastic deformation of the inner cylinder member 10, which consequently causes the engagement pieces 31 to displace in diameter expansion directions or diameter shrinking directions.

The inner peripheral surface of the engagement plate 30 is formed such that the six engagement pieces 31 forms a hexagonal area when viewed in the axial direction. The six slits 11 are formed so as to extend through positions corresponding to the angles of the hexagon formed by the engagement plate 30. While the outer cylinder member 40 is mounted on the inner cylinder member 10, the inner peripheral end portion of the engagement plate 30 engages with the recess 7 of the aperture section 5. The size of the hexagon formed by the inner peripheral surface of the engagement plate 30 is not particularly limited, provided that the smallest diameter of the engagement plate 30 is smaller than the largest diameter of the bottom of the recess 7, while the outer cylinder member 40 is mounted to the inner cylinder member 10.

By having the engagement plate 30 engaged with the recess 7, a movement of the inner cylinder member 10 in a circumferential direction or the axial direction relative to the syringe main body 3 is restricted. More specifically, by having the inner peripheral surface of the engagement plate in a hexagon shape fit together with the bottom of the recess 7 in a hexagon shape, a movement in the circumferential direction is restricted. Further, with the engagement plate 30 interposed in the axial direction between side surfaces of the recess 7, a movement in the axial direction is restricted. With a movement in the circumferential direction restricted, the female screw 21 of the inner cylinder member 10 is prevented from rotating along with a male screw of the other member, when the female screw 21 is screw-fastened with the male screw.

Figure 6:
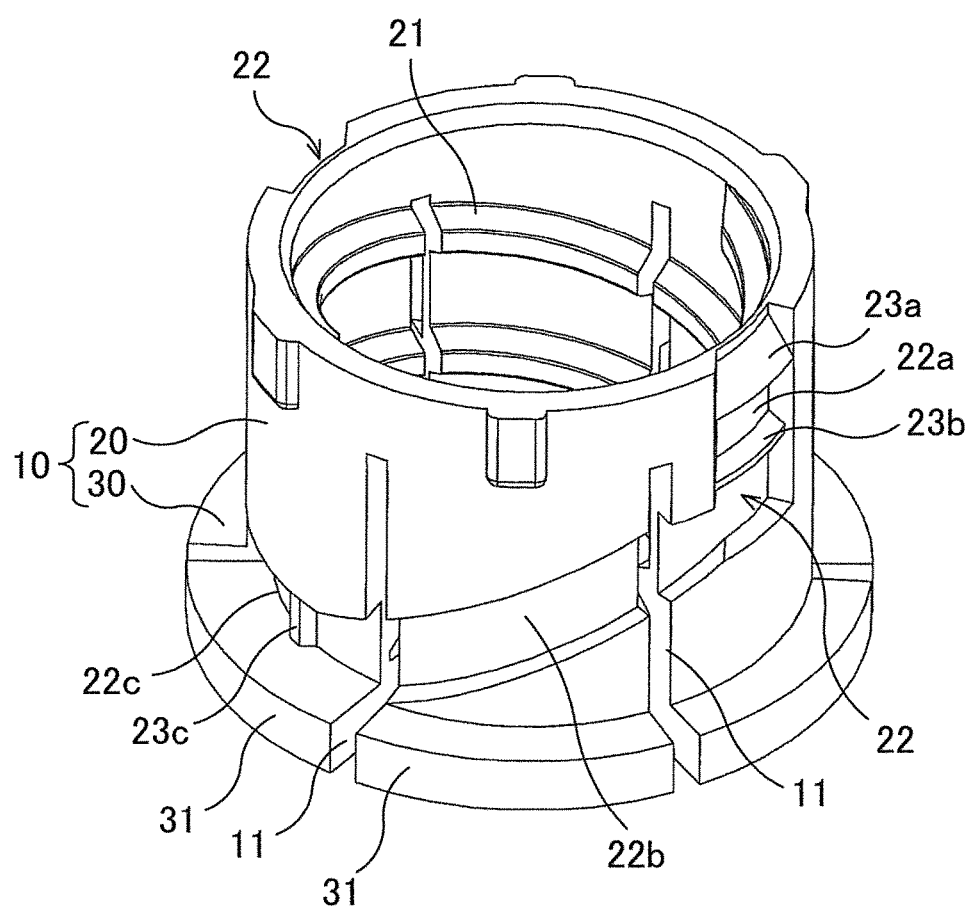
FIG. 6 is an exploded perspective view of an inner cylinder member shown in FIG. 1.

As shown in FIG. 6, the outer peripheral surface of the inner cylinder body 20 is provided with two engagement grooves 22. The two engagement grooves 22 are formed in positions of 180 degrees from each other. With the two engagement grooves 22 are engaged with two engagement protrusions 42 which are formed on the inner peripheral surface of the outer cylinder member 40, in positions of 180 degrees from each other. Each of the engagement grooves 22 includes a first groove portion 22a, a second groove portion 22b, and a third groove portion 22c.

The first groove portion 22a extends in the axial direction, from the front end of the outer peripheral surface of the inner cylinder body 20 (see FIG. 3, FIG. 6). The second groove portion 22b is formed in helical shape which extends from the trailing end of the first groove portion 22a towards back (see FIG. 4, FIG. 6). The third groove portion 22c extends in a circumferential direction, from the trailing end of the second groove portion 22b (see FIG. 2, FIG. 4). The third groove portion 22c is provided at the trailing end of the outer peripheral surface of the inner cylinder body 20. The front surface of the engagement plate 30 forms one of the side surfaces of the third groove portion 22c. While the outer cylinder member 40 is mounted on the inner cylinder member 10, the engagement protrusion 42 of the outer cylinder member 40 is interposed by both side surfaces of the third groove portion 22c in the axial direction, and engages with the third groove portion. This way, the movement of the outer cylinder member 40 in the axial direction relative to the inner cylinder member 10 is restricted.

The first groove portion 22a is provided with a projection 23a and a projection 23b each protruding outwardly in a radial direction, which are aligned in the axial direction (see FIG. 3, FIG. 6). In an end portion of the third groove portion 22c close to the second groove portion 22b is provided a projection 23c protruding outwardly in a radial direction (see FIG. 4, and FIG. 6). The projection 23a has substantially a triangular cross section with one of its side parallel to the axial direction. The back surface of the projection 23a is substantially perpendicular to the axial direction. The protrusion-heights of the projection 23b and the projection 23c are lower than that of the projection 23a. The projection 23b is tapered and has substantially a trapezoidal cross section relative to the axial direction. The side surfaces on both sides are tilted with respect to the axial direction. The projection 23c has substantially a trapezoidal cross section relative to the circumferential direction. The side surfaces on both sides are tilted with respect to a radial direction.

The outer cylinder member 40 is provided for preventing the inner peripheral end of the engagement plate 30 of the inner cylinder member 10 from being detached from the recess 7. The outer cylinder member 40 is mounted to the inner cylinder member 10 from the front end of the inner cylinder member 10.

The trailing end of the outer cylinder member 40 fits together with the outer peripheral surface of the engagement plate 30 of the inner cylinder member 10. Of the inner peripheral surface of the outer cylinder member 40, a portion to contact the outer peripheral surface of the engagement plate 30 is hereinafter referred to as contact surface 41. With the contact surface 41 contacting the outer peripheral surface of the engagement plate 30, the engagement pieces 31 are restricted from displacing in diameter expansion directions. Therefore, the engagement plate 30 is prevented from being detached from the recess 7. As the result, the connection member 2 is not easily detached from the aperture section 5, and hence, unintentional disconnection of the connection member 2 is prevented.

By making the diameter of the contact surface 41 smaller than the outer diameter of the engagement plate 30 of the inner cylinder member 10 while the outer cylinder member 40 is not mounted, the engagement plate 30 is pressed in radial directions by the contact surface 41 when the outer cylinder member 40 is mounted to the inner cylinder member 10. This causes elastic deformation of the inner cylinder member 10, and with the force of the inner cylinder member 10 to restore its original shape, the outer cylinder member 40 and the inner cylinder member 10 are firmly attached to each other. It should be noted that the diameter of the contact surface 41 may be the same as the outer diameter of the engagement plate 30 of the inner cylinder member 10 while the outer cylinder member 40 is not mounted.

As shown in FIG. 2 and FIG. 5, the inner peripheral surface of the outer cylinder member 40 is provided with two engagement protrusions 42 which engages with the two engagement grooves 22 of the inner cylinder member 10. The engagement protrusions 42 are provided on the front side of the contact surface 41 of the outer cylinder member 40. A cross section of each engagement protrusion 42 in a radial direction, and a cross section of the same perpendicular to the axial direction both have substantially a trapezoidal shape. The front surface of the engagement protrusion 42 is substantially perpendicular to the axial direction, and the side surfaces other than the front surface of the engagement protrusion 42 are tilted to form a tapered shape of the engagement protrusion 42.

Further, the outer peripheral surface of the outer cylinder member 40 is provided with a plurality of ribs 43 in the axial direction. These ribs 43 have a function of preventing slipping when the outer cylinder member 40 is held by fingers.

The following describes steps of detaching the connection member 2 from the syringe main body 3.

First, the outer cylinder member 40 is rotated relative to the inner cylinder member 10 and the aperture section 5 so that each engagement protrusion 42 moves towards the projection 23c. The engagement protrusion 42 then climbs over the projection 23c, and is positioned in the second groove portion 22b. Next, the outer cylinder member 40 is helically rotated towards front so that each engagement protrusion 42 moves along the second groove portion 22.

Figure 7:
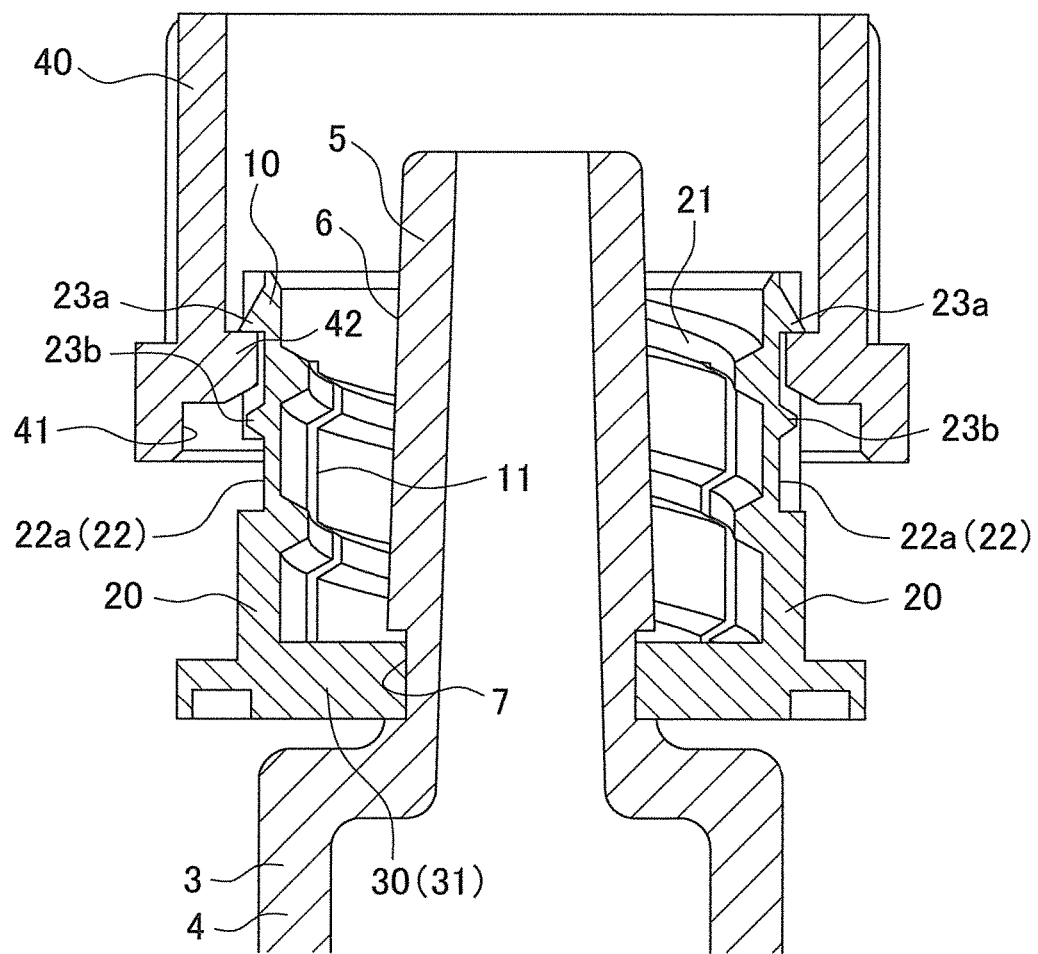
FIG. 7 is a cross sectional view showing the connection member of FIG. 1 being detached from the syringe main body.

When each of the engagement protrusions 42 climbs to the trailing end of the first groove portion 22a and contacts the side surface of the first groove portion 22, the outer cylinder member 40 is moved towards front. The engagement protrusion 42 then moves over the projection 23b, and is stopped by the projection 23a, as shown in FIG. 7. Therefore, the outer cylinder member 40 is not detached from the inner cylinder member 10. Further, the projection 23b at the back side of the engagement protrusion 42 prevents the engagement protrusion 42 from returning to the second groove portion 22b, even when the outer cylinder member 40 is released from a hand.

While the engagement protrusion 42 is held between the projection 23a and the projection 23b, application of a frontward force to the outer cylinder member 40 or the inner cylinder member 10 causes elastic deformation of the inner cylinder member 10, thereby causes the inner peripheral end of the engagement plate 30 to depart the recess 7. Consequently, the inner cylinder member 10 and the outer cylinder member 40 are detached from the aperture section 5.

Further, to attach the connection member 2 to the syringe main body 3 in manufacturing of the syringe 1, the aperture section 5 of the syringe main body 3 is first inserted into a hole at the center of the engagement plate 30 of the inner cylinder member 10, and the inner cylinder member 10 is moved towards back relative to the aperture section 5. The engagement pieces 31 pressed in radial directions by the outer peripheral surface of the aperture section 5 are displaced in the diameter expansion directions, and positioned to the recess 7.

Next, the outer cylinder member 40 is positioned to cause the back surface of each engagement protrusion 42 of the outer cylinder member 40 to contact the front surface of the projection 23a of the engagement groove 22 of the inner cylinder member 10, and then a backward force is applied to the outer cylinder member 40. This way, the engagement protrusion 42 climbs over the projection 23a, and is positioned between the projection 23a and the projection 23b. After that, the steps for detaching the connection member 2 are carried out in the reverse sequence.

The syringe 1 of the present embodiment brings about the following effects.

The outer cylinder member 40 positioned outermost of the connection member 2 is attached to the inner cylinder member 10 by having its inner peripheral surface fit together with the inner cylinder member 10. Further, to detach the connection member 2 from the aperture section 5, the outer cylinder member 40 needs to be moved in the axial direction relative to the inner cylinder member 10. While the outer cylinder member 40 is mounted to the inner cylinder member 10, the engagement pieces 31 of the inner cylinder member 10 are restricted from displacing in the diameter expansion directions, keeping the engagement pieces 31 engaged with the recess 7. This prevents the inner cylinder member 10 from being detached from the aperture section 5. Therefore, the connection member 2 will not be detached from the aperture section 5 simply by holding the connection member 2 with a hand, or by the connection member 2 hitting the other instrument. Therefore, unintentional disconnection of the connection member 2 is prevented.

Further, the outer cylinder member 40 and the inner cylinder member 10 are less likely to be broken than traditional connection members with arms extended in the axial direction, because they do not have a portion protruding in the axial direction.

Further, since the inner peripheral surface of the outer cylinder member 40 contacts the outer peripheral surface of the engagement plate 30, the engagement plate 30 and the recess 7 are firmly engaged.

Further, the outer cylinder member 40 is attached to the inner cylinder member 10 by fitting the inner peripheral surface of the outer cylinder member 40 together with the inner cylinder member 10 and engaging the engagement protrusions 42 with the engagement grooves 22 of the inner cylinder member 10. This makes it more difficult to detach the outer cylinder member 40 from the inner cylinder member 10, as compared with cases where the outer cylinder member 40 is attached to the inner cylinder member simply by fitting the outer cylinder member 40 together with the inner cylinder member 10. Therefore, unintentional disconnection of the outer cylinder member 40 is prevented.

Further, while the outer cylinder member 40 is mounted to the inner cylinder member 10, each of the engagement protrusions 42 is interposed in the axial direction, in the third groove portion 22c formed in the circumferential direction. This restricts a movement of the outer cylinder member 40 in the axial direction relative to the inner cylinder member 10. Therefore, even when the outer cylinder member 40 is pulled in the axial direction, the outer cylinder member 40 is not detached from the inner cylinder member 10, and hence, unintentional disconnection of the outer cylinder member 40 is prevented.

Further, while the outer cylinder member 40 is mounted to the inner cylinder member 10, each of the engagement protrusions 42 faces the projection 23c in circumferential directions. This makes it difficult to rotate the outer cylinder member 40 relative to the inner cylinder member 10, which prevents unintentional disconnection of the connection member 2. Further, when loosening the outer cylinder member 40 and the inner cylinder member 10, each of the engagement protrusions 42 first climb over the projection 23c. This provides a user a feeling of operation.

Further, when detaching the connection member 2, each of the engagement protrusions 42 held between the projection 23a and the projection 23b is kept from returning to the second groove portion 22b. Therefore, the outer cylinder member 40 does not hinder displacement of the engagement pieces 31 in the diameter expansion directions.

Further, in the present embodiment, the six slits 11 of the connection member 2 are provided to extend through positions corresponding to angles of a hexagon formed by the inner peripheral surface of the engagement plate 30. As such, the inner peripheral surface of each engagement piece 31 forms one side of the hexagon. Since the inner peripheral surface of each engagement piece 31 is flat, the inner cylinder member 10 is easily manufacturable.

Embodiment 2

Next, the following describes Embodiment 2 of the present invention. Members and parts similar to those of Embodiment 1 are given the same reference numerals, and description for those members and parts are omitted where appropriate.

Figure 8:
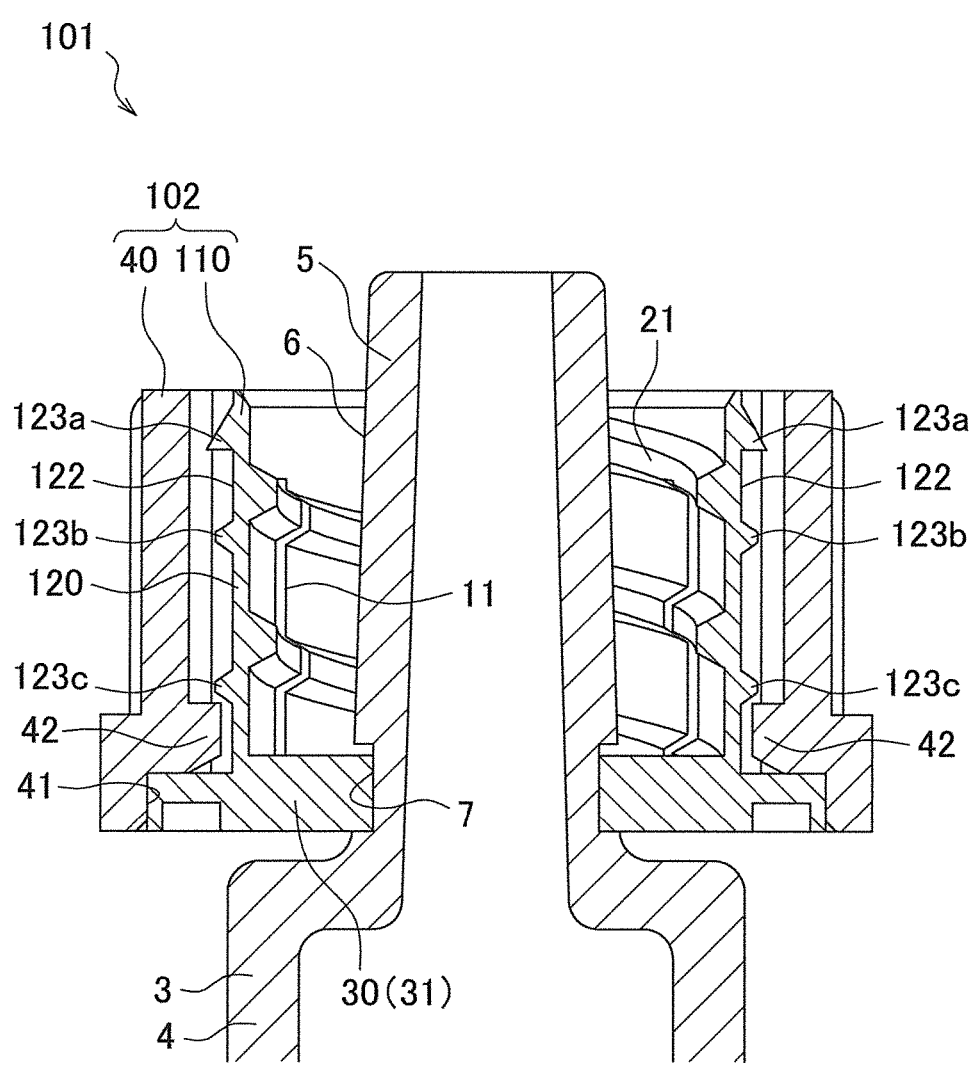
FIG. 8 is a cross sectional view of a syringe related to Embodiment 2 of the present invention.
Figure 9:
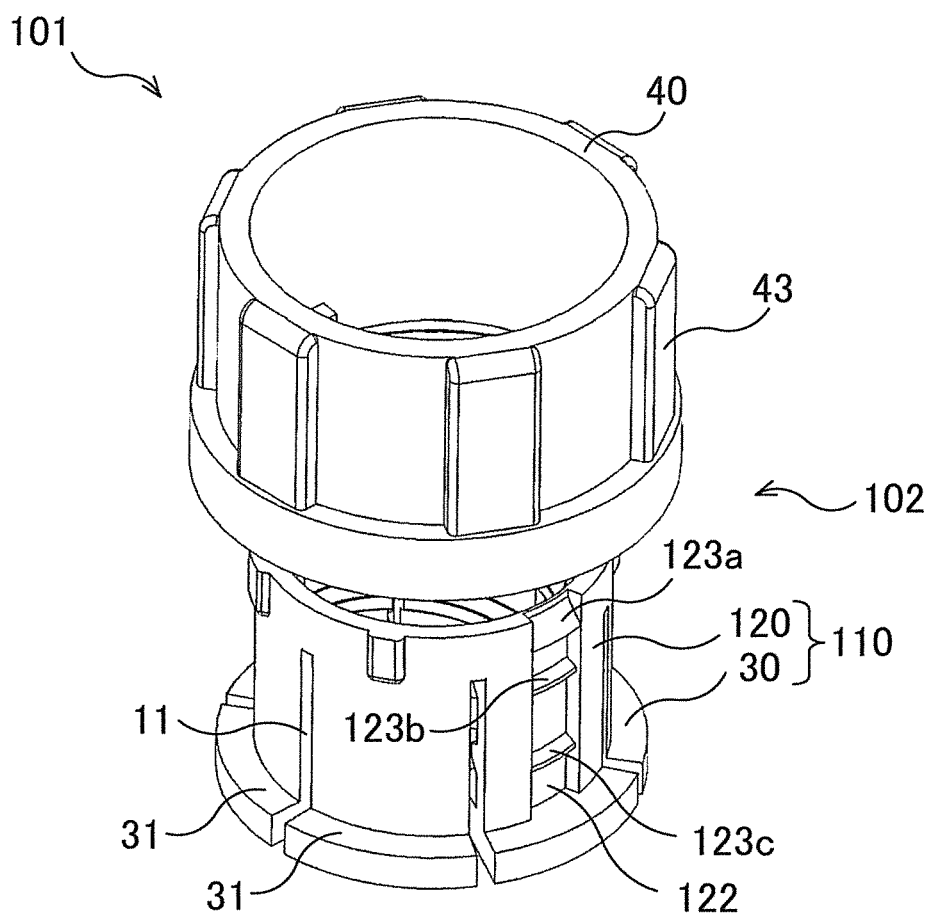
FIG. 9 is an exploded perspective view of a syringe shown in FIG. 8.
Figure 9:
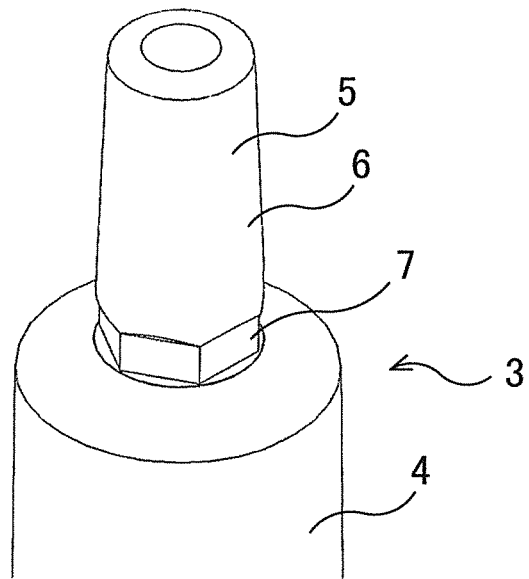

As shown in FIG. 8 and FIG. 9, a syringe 101 of the present embodiment has the same structure as that of Embodiment 1, except in that the structure of an inner cylinder member of the connection member is different from that of Embodiment 1.

The inner cylinder member 110 of the present embodiment has a substantially cylindrical inner cylinder body 120 and an engagement plate 30 formed at the trailing end of the inner cylinder member 120. To the inner cylinder member 110 are provided six slits 11 as in the case of Embodiment 1.

The outer peripheral surface of the inner cylinder body 120 is provided with two engagement grooves 122. The two engagement grooves 122 are formed in positions of 180 degrees from each other. The engagement grooves 122 each extends in the axial direction, from the front end of the outer peripheral surface of the inner cylinder body 120. With the two engagement grooves 122 are engaged with two engagement protrusions 42 which are formed on the inner peripheral surface of the outer cylinder member 40.

Each of the engagement grooves 122 has 3 projections 123a, 123b, and 123c which protrude outwardly in a radial direction. These three projections 123a, 123b, and 123c are aligned in axial direction. The projection 123a has the same shape as the projection 23a of Embodiment 1. The projections 123b and 123c have the same shape as the projection 23b of Embodiment 1. While the outer cylinder member 40 is mounted on the inner cylinder member 110, each of the engagement protrusions 42 of the outer cylinder member 40 is between the projection 123c and the top surface of an engagement piece 31. Therefore, a movement of the outer cylinder member 40 in the axial direction relative to the inner cylinder member 110 are restricted.

To detach the connection member 102 from the syringe main body 3, a frontward force is first applied to the outer cylinder member 40. The engagement protrusion climbs over the projection 123c, 123b, and is positioned between the projection 123b and the projection 123a. Then, application of the frontward force to the outer cylinder member 40 or the inner cylinder member 110 causes elastic deformation of the inner cylinder member 110 and the inner peripheral end of the engagement plate 30 is detached from the recess 7, thus separating the inner cylinder member 110 and the outer cylinder member 40 from the aperture section 5.

Therefore, as in the case of the syringe 1 of Embodiment 1, with the syringe 101 of the present embodiment, the connection member 102 will not be detached from the aperture section 5 simply by holding the connection member 102 with a hand, or by the connection member 102 hitting the other instrument. Therefore, unintentional disconnection of the connection member 2 is prevented. Further, the connection member 102 is less likely to be broken than traditional connection members with arms extended in the axial direction, because it does not have a portion protruding in the axial direction.

Further, with the engagement grooves 122 formed in the axial direction, the outer cylinder member 40 is detached from or attached to the inner cylinder member 110, simply by moving the outer cylinder member 40 in the axial direction, relative to the inner cylinder member 110. Therefore, attachment and detachment are facilitated.

Further, while the outer cylinder member 40 is mounted to the inner cylinder member 110, the front surface of each of the engagement protrusions 42 faces the projection 123c in the axial direction. This makes it difficult to move the outer cylinder member 40 relative to the inner cylinder member 110, which prevents unintentional disconnection of the connection member 102. Further, when loosening the outer cylinder member 40 and the inner cylinder member 110, each of the engagement protrusions 42 first climb over the projection 123c. This provides a user a feeling of operation.

Embodiment 3

Next, the following describes Embodiment 3 of the present invention. Members and parts similar to those of Embodiment 1 or Embodiment 2 are given the same reference numerals, and description for those members and parts are omitted where appropriate.

Figure 10:
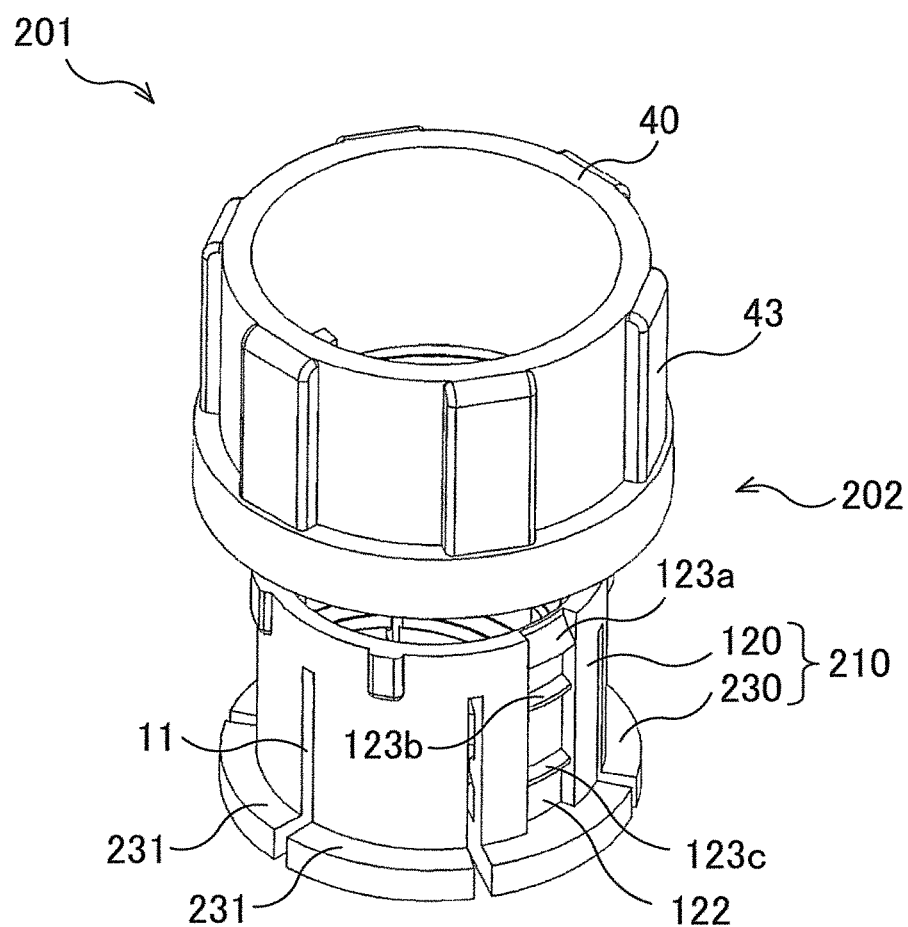
FIG. 10 is an exploded perspective view of a syringe related to Embodiment 3 of the present invention.
Figure 10:
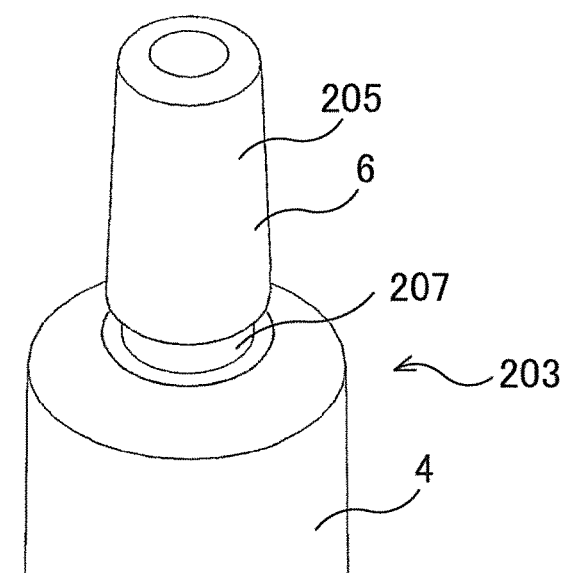
Figure 11:
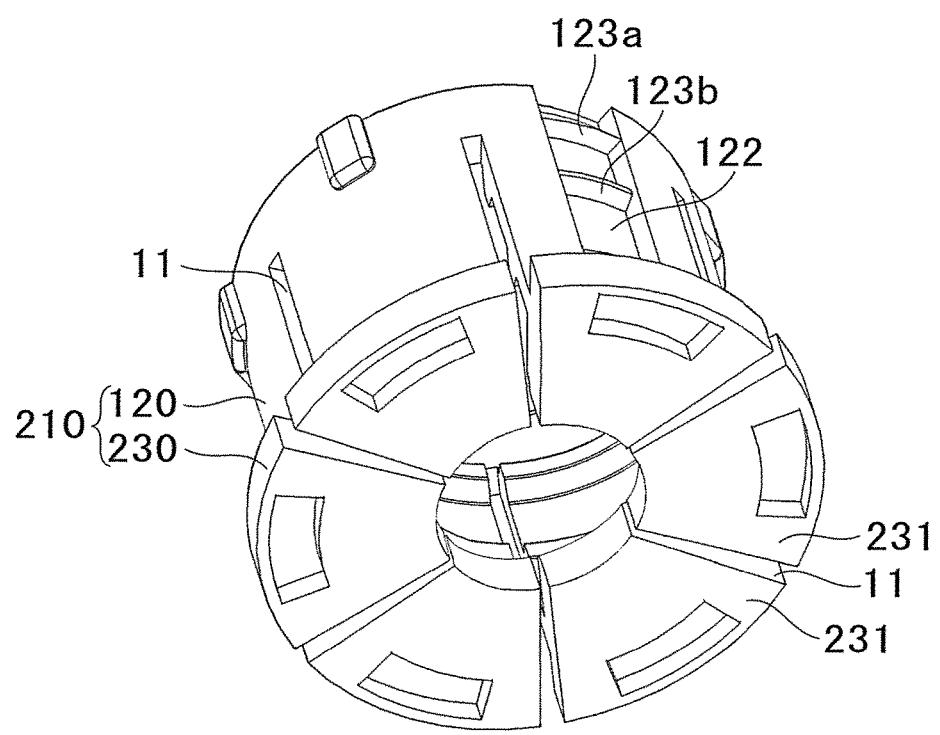
FIG. 11 is a perspective view of an inner cylinder member shown in FIG. 10.

As shown in FIG. 10 and FIG. 11, a syringe 201 of the present embodiment has the same structure as that of Embodiment 2, except in that the shape of an aperture section 205 of a syringe main body 203, and the shape of an engagement plate 230 of an inner cylinder member 210 of a connection member 202 are different from those of Embodiment 2.

Further, the aperture section 205 has an annular recess 207 at its outer peripheral surface, on the back side of a male luer taper 6. The bottom surface of the recess 207 forms a circle, when viewed in the axial direction.

The engagement plate 230 is divided into six fan-shaped engagement pieces 231, by six slits 11. The inner peripheral surface of the engagement plate 230 is formed such that the six engagement pieces 231 forms a circular area when viewed in the axial direction. The engagement plate 230 is the same as the engagement plate 30 except in the shape its inner peripheral surface forms.

The inner peripheral end of the engagement plate 230 engages with the recess 207 of the aperture section 205. This way, a movement of the inner cylinder member 210 in the axial direction relative to the syringe main body 203 is restricted. Further, while the engagement plate 230 is engaged with the recess 207, the inner cylinder member 210 is rotatable relative to the syringe main body 203. Thus, although, when screw-fastening the male screw of another member (not shown) to the female screw 21 of the inner cylinder member 210, the connection member 202 needs to be held to prevent the rotation of inner cylinder member 210 along with the male screw, it is possible to rotate the inner cylinder member 210 to bring it to a position that facilitates screw-fastening before starting the connection work. Therefore, the connection work is made easy.

Further, while the engagement plate 230 is engaged with the recess 207 of the aperture section 205, and a contact surface 41 of the outer cylinder member 40 is engaged with the outer peripheral surface of the engagement plate 230, the inner peripheral surface of the engagement plate 230 is preferably pressed against the bottom of the aperture section 205; however, the inner peripheral surface of the engagement plate 230 may be in contact with the bottom surface of the aperture section 205, without being pressed against the bottom surface. Further, if the inner diameter of the engagement plate 230 is smaller than the diameter of the trailing end of the male luer taper 6, the inner peripheral surface of the engagement plate 230 does not have to be in contact with the bottom surface of the aperture section 205. Pressing the inner peripheral surface of the engagement plate 230 against the bottom surface of the aperture section 205 makes it difficult to rotate the inner cylinder member 210 relative to the syringe main body 203. Therefore, once the syringe 201 is connected to another instrument (not shown), the connection member 202 is kept from loosening even when it hits the other instrument.

The steps for detaching the connection member 202 from the syringe main body 203 are the same as those of Embodiment 2. Further, the effects brought about by the syringe 201 of the present embodiment are the same as those brought about by the syringe 101 of Embodiment 2, except for the above described effects related to the shape of the inner peripheral surface of the recess 207 of the aperture section 205 and the shape formed by the inner peripheral surface of the engagement plate 230.

Thus, preferable embodiments of the present invention have been described hereinabove. It should be noted that the present invention is not limited to the thus described embodiments, and various modifications are possible within the scope of appended claims. Modifications described below may be implemented in combinations.

The above Embodiments 1 to 3 each deals with a case where the engagement plate (30, 230) is provided at the trailing end of the inner cylinder member (10, 110, 210); however, the engagement plate (30, 230) may be provided in a midway portion of the inner cylinder member (10, 110, 210) relative to the axial direction, as long as it is on the back side of the female screw 21.

Figure 12:
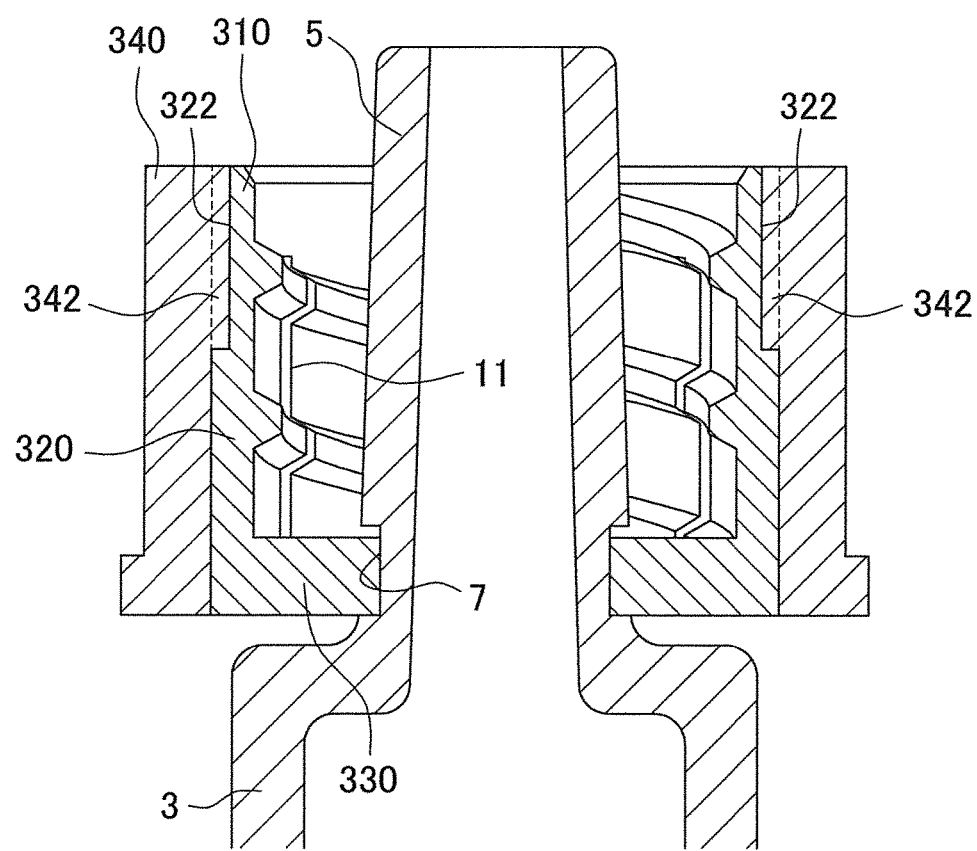
FIG. 12 is a cross sectional view of a syringe related to another embodiment of the present invention.

The above Embodiments 1 to 3 each deals with a case where the outer peripheral end of the engagement plate (30, 230) protrude from the outer peripheral surface of the inner cylinder body (20, 120); however, as shown in FIG. 12 for example, it is possible to adopt a structure in which the outer peripheral end of an engagement plate 330 not protruding from the outer peripheral surface of an inner cylinder body 320.

The above Embodiments 1 to 3 each deals with a case where the inner peripheral surface of the outer cylinder member contacts the outer peripheral surface of the engagement plate of the inner cylinder member; however, the position at which the outer cylinder member contacts the inner cylinder member may be any given position as long as it is within a range of the plurality of slits 11, relative to the axial direction. For example, it is possible to adopt a structure shown in FIG. 12, in which substantially the entire inner peripheral surface of an outer cylinder member 340 contacts the outer peripheral surface of an inner cylinder member 310.

Further, for example, the outer peripheral surface of the inner cylinder member may be provided with an annular protrusion in a position different from the engagement plate relative to the axial direction, and the leading end of this protrusion may be in contact with the inner peripheral surface of the outer cylinder member.

In any of the above Embodiment 1 to Embodiment 3, there are six slits 11; however, the number and the positions of the slits 11 are not limited to those described in the above embodiments. The slits 11 simply need to be radially formed when viewed in the axial direction.

The projection (23b, 123b) does not necessarily have to be provided.

The above Embodiments 1 to 3 each deals with a case where the engagement protrusion 42 hits and is stopped by the projection (23a, 123a), so that the outer cylinder member 40 is not detached from the inner cylinder member (10, 110) at a time of detaching the connection member (2, 102, 202); however, it is possible to adopt a structure in which the outer cylinder member is detached from the inner cylinder member. In other words, the projection (23a, 123a) does not necessarily have to be provided. In such a case, the projection (23b, 123b) does not necessarily have to be provided either.

The above Embodiments 1 to 3 each deals with a case where the projection (23c, 123c) which faces the engagement protrusion 42 while the outer cylinder member 40 is mounted to the inner cylinder member (10, 110, 210) is provided in the engagement grooves (22, 122); however, the projection (23c, 123c) does not necessarily have to be provided. For example, the lengths of the engagement protrusion 42 and the third groove portion 22c of the engagement groove 22 may be made substantially the same, and the engagement protrusion 42 may be fit into the third groove portion 22c. This way, the connection member 2 is hardly detached, even without the projection 23c.

In a case shown in FIG. 12, where an engagement groove 322 extending in the axial direction has no projection, the length of the engagement protrusion 342 of the outer cylinder member 340 may be made substantially the same as the length of the engagement groove 322 relative to the axial direction.

The above Embodiments 1 to 3 each deals with a case where the number of engagement grooves (22, 122) is 2; however, the number of the engagement grooves (22, 122) may be 1 or 3 or more.

In the above Embodiment 1 and Embodiment 2, the bottom surface of the recess 7 forms a hexagon when viewed in the axial direction; however, the bottom surface may form any polygonal shape other than a hexagon.

In the above Embodiment 1 and Embodiment 2, an area surrounded by the six engagement pieces 31 of the engagement plate 30 has the same hexagon shape as that formed by the bottom surfaces of the recess 7, when viewed in the axial direction. However, the shape formed by the inner peripheral surface of the engagement plate 30 may be different from that formed by the bottom surface of the recess 7, provided that the engagement plate 30 fits together with the recess 7.

In the above Embodiment 1, the engagement grooves 22 are each structured by the first groove portion 22a extending in the axial direction, the second groove portion 22b extended helically, and the third groove portion 22c extended in a circumferential direction; however, the shape of the groove extended towards front from the portion of the groove extended in the circumferential direction is not limited to that of Embodiment 1. For example, the engagement groove may include only a portion that extends in the axial direction and a portion that extends in the circumferential direction, from the trailing end of the portion extended in the axial direction. Further for example, the engagement groove may include only a portion that extends in helically and a portion that extends in the circumferential direction, from the trailing end of the helically extended portion. While the outer cylinder member is mounted to the inner cylinder member, the engagement protrusion 42 is positioned in the portion of the engagement groove extended in the circumferential direction.

The engagement protrusion 42 and the engagement groove (22, 122) do not necessarily have to be provided.

Figure 13:
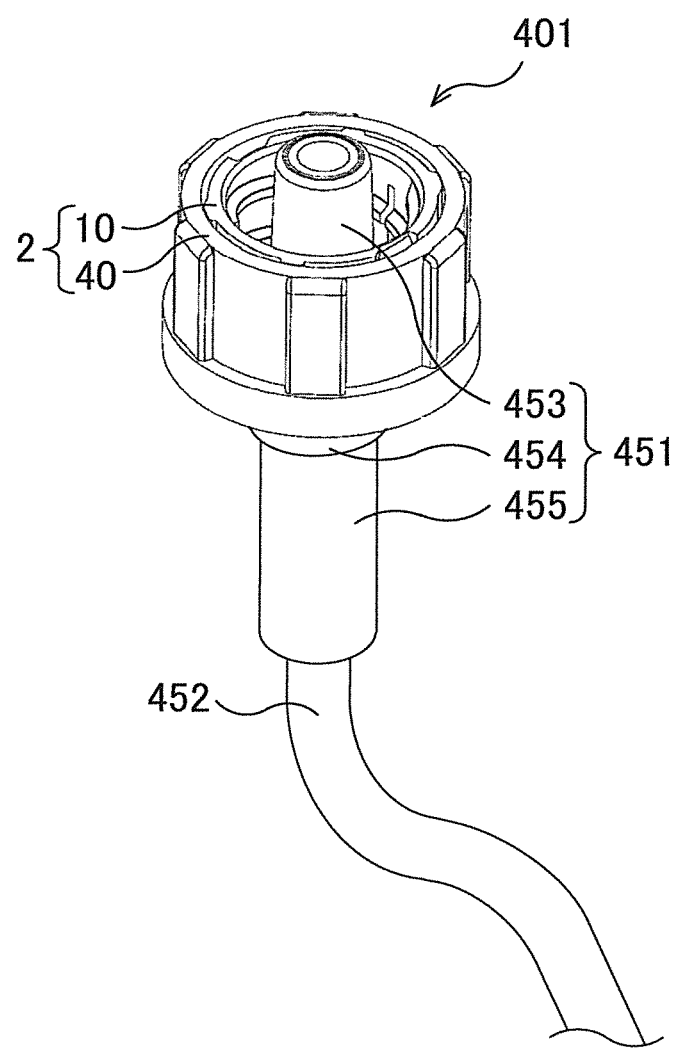
FIG. 13 is a cross sectional view of a catheter related to another embodiment of the present invention.
Figure 14:
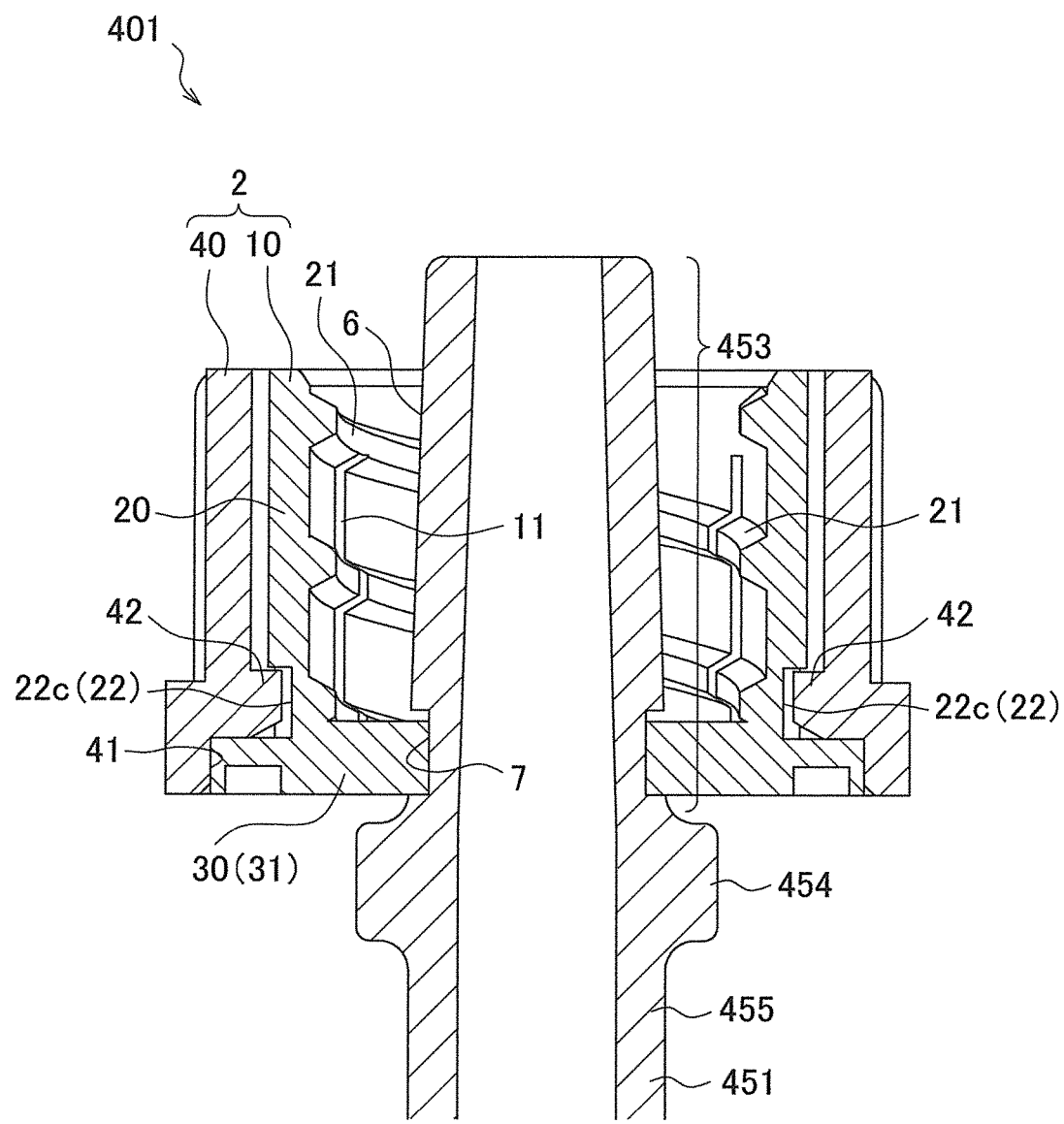
FIG. 14 is a cross sectional view of a catheter shown in FIG. 13.

Applicable medical instrument of the connector of the present invention for a fluid is not limited to syringes. The connector of the present invention for a fluid is applicable to, for example, a catheter shown in FIG. 13, an administration set, a blood infusion set, and the like. The catheter 401 shown in FIG. 13 includes: a cylindrical member 451, a connection member 2, and a flexible tube 452 jointed to the cylindrical member 451. As shown in FIG. 14, the cylindrical member 451 has a front cylindrical section (cylindrical section) 453 having a shape similar to the aperture section 5, a large-diameter section 454, and a back cylindrical section 455. The outer diameter of the large-diameter portion 454 is greater than the outer diameter of the front cylindrical section 453, to prevent the connection member 2 from moving towards the back cylindrical section 455, at a time of detaching the connection member 2 from the cylindrical member 451. The front cylindrical section 453 of the cylindrical member 451 and the connection member 2 structure a connector of the present invention for a fluid.

REFERENCE SIGN LISTING 1, 101, 201: Syringe
2, 102, 202: Connection Member
3, 203: Syringe Main Body
4: Body Section
5, 205: Aperture Section (Cylindrical Section)
6: Male Lure Taper
7, 207: Recess
10, 110, 210, 310: Inner Cylinder Member
11: Slit
20, 120, 320: Inner Cylinder Body
21: Female Screw
22, 122, 322: Engagement Groove
22a: First Groove Portion
22b: Second Groove Portion
22c: Third Groove Portion
23a, 23b, 23c, 123a, 123b, 123c: Protrusion
30, 230, 330: Engagement Plate
31, 231: Engagement Piece
40, 340: Outer Cylinder Member
41: Contact Surface
42, 342: Engagement Protrusion
43: Rib
401: Catheter
451: Cylindrical Member
453: Front Cylindrical Section (Cylindrical Section)

The invention claimed is:

1. A connector for a fluid, comprising: a cylindrical section configured to let a fluid pass therethrough, which has a male luer taper at a distal end portion of its outer peripheral surface;
  a connection member detachably attached to the cylindrical section, which is used in connecting with another member having, on its inner peripheral surface, a female luer taper,
  wherein the cylindrical section has, on an outer peripheral surface of a proximal other end portion, an annular recess,
  wherein the connection member comprises
  an inner cylinder member coaxial with the cylindrical section, which is mountable to the cylindrical section in such a manner that the cylindrical section is at least partially accommodated inside the inner cylinder member, and
  an outer cylinder member which is coaxial with the inner cylinder member, and which is mountable to the inner cylinder member in such a manner that the inner cylinder member is at least partially accommodated inside the outer cylinder member, the outer cylinder member being fittable, with the inner cylinder member in such a manner that the outer cylinder member is moved from the distal end portion of the cylindrical section toward the proximal other end portion of the cylindrical section with respect to the inner cylinder member mounted to the cylindrical section,
  wherein the inner cylinder member comprises
  an inner cylinder body having on its inner peripheral surface a female screw, and
  an engagement plate configured to engage with the annular recess and connect with the inner cylinder body at a position farther from the distal end portion of the cylindrical section than the female screw is from the distal end portion, relative to an axial direction of the cylindrical section,
  wherein the inner cylinder member is provided with a plurality of slits which are arranged radially with respect the axial direction of the cylindrical section, and which extend from the engagement plate to a part of the inner cylinder body so as to divide the engagement plate into a plurality of engagement pieces, and partially divide the inner cylinder body into segments corresponding to the plurality of engagement pieces,
  wherein a movement of the inner cylinder member in the axial direction of the cylindrical section relative to the cylindrical section is restricted by engagement of the annular recess with the engagement plate,
  wherein, when the outer cylinder member is not mounted to the inner cylinder member, the plurality of engagement pieces are displaceable in diameter expansion directions as a result of elastic deformation of the inner cylinder member when a radial force is applied to the engagement plate, and
  wherein, when the outer cylinder member is mounted to the inner cylinder member, an inner peripheral surface of the outer cylinder member contacts an outer peripheral surface of the inner cylinder member within a range of the plurality of slits, relative to the axial direction of the cylindrical section, thereby restricting displacement of the plurality of engagement pieces in the diameter expansion directions.

2. The connector according to claim 1, wherein a bottom surface of the annular recess forms a polygonal shape when viewed in the axial direction of the cylindrical section, and movements of the inner cylinder member in a circumferential direction and in the axial direction of the cylindrical section, relative to the cylindrical section are restricted by having the annular recess engaged with the engagement plate.

3. The connector according to claim 2, wherein an area surrounded by the plurality of engagement pieces has a polygonal shape when viewed in the axial direction of the cylindrical section, and
  the plurality of slits are formed in positions corresponding to angles of the polygonal shape.

4. The connector according to claim 1, wherein a bottom surface of the annular recess forms a circular shape when viewed in the axial direction of the cylindrical section.

5. The connector according to claim 1, wherein the inner peripheral surface of the outer cylinder member contacts an outer peripheral surface of the engagement plate, when the outer cylinder member is mounted to the inner cylinder member.

6. The connector according to claim 1, wherein the inner peripheral surface of the outer cylinder member is provided with at least one engagement protrusion, and
  the outer peripheral surface of the inner cylinder member is provided with at least one engagement groove which engages with said at least one engagement protrusion.

7. The connector according to claim 6, wherein each of the at least one engagement groove has a portion formed in a circumferential direction, and each of the at least one engagement protrusion is positioned in the portion of each of the at least one engagement groove when the outer cylinder member is mounted to the inner cylinder member.

8. The connector according to claim 7, wherein each of the at least one engagement groove has a projection which protrudes outwardly in a radial direction and is configured to face each of the at least one engagement protrusion relative to the circumferential direction, when the outer cylinder member is mounted to the inner cylinder member, and the projection is designed so as to allow each of the at least one engagement protrusion to climb over the projection by moving, in the circumferential direction relative to the inner cylinder member, the outer cylinder member mounted to the inner cylinder member.

9. The connector according to claim 6, wherein each of the at least one engagement groove is formed in the axial direction of the cylindrical section.

10. The connector according to claim 9, wherein each of the at least one engagement groove has a projection which protrudes outwardly in a radial direction and is configured to face each of the at least one engagement protrusion relative to the axial direction of the cylindrical section when the outer cylinder member is mounted to the inner cylinder member, and the projection is designed so as to allow each of the at least one engagement protrusion to climb over the projection by moving, in the axial direction of the cylindrical section relative to the inner cylinder member, the outer cylinder member mounted to the inner cylinder member.

11. A syringe having the connector according to claim 1 for a fluid, comprising:
- a syringe main body having a cylindrical body section having a distal end, and the cylindrical section having the proximal other end portion which connects a center of the distal end of the body section; and
- the connection member.

* * * * *